United States Patent [19]

Vargas et al.

[11] Patent Number: 5,382,715
[45] Date of Patent: Jan. 17, 1995

[54] HYDROGENATION CATALYST WITH LOW PHOSPHOROUS CONTENT FOR OXO ALCOHOL PROCESS

[75] Inventors: Jose M. Vargas; Kenneth L. Riley, both of Baton Rouge, La.

[73] Assignee: Exxon Chemical Patents Inc., Linden, N.J.

[21] Appl. No.: 159,099

[22] Filed: Nov. 29, 1993

[51] Int. Cl.⁶ .............. C07C 29/141; C07C 31/125; C07C 29/16
[52] U.S. Cl. .................... 568/882; 568/914
[58] Field of Search ................ 568/882, 914

[56] References Cited

U.S. PATENT DOCUMENTS 2,876,264  3/1959  Brodkey et al. ............ 568/882
4,426,541  1/1984  King ...................... 568/882
5,030,774  7/1991  Oswald et al. ............. 568/882

FOREIGN PATENT DOCUMENTS 343819  11/1989  European Pat. Off. .

OTHER PUBLICATIONS

Kirk–Othmer, Encyclopedia of Chemical Technology, Third Edition, vol. 16, John Wiley & Sons, pp. 637–653, 1981, OXO PROCESS.

Primary Examiner—Joseph E. Evans
Attorney, Agent, or Firm—J. J. Mahon

[57] ABSTRACT

The hydrogenation steps and hydrofinishing steps of the cobalt catalyst oxo process for preparation of the alcohols by the hydroformylation of olefin are carried out using a nickel-molybdenum catalyst on an alumina or silica alumina support which has a phosphorous content of 0.1 wt. % to 1.0 wt. % phosphorus.

4 Claims, No Drawings

HYDROGENATION CATALYST WITH LOW PHOSPHOROUS CONTENT FOR OXO ALCOHOL PROCESS

This invention relates to an improved process for preparing alcohols by the oxo process. More particularly this invention relates to an improvement in the hydrogenation step of the oxo process characterized in the use of certain bimetallic hydrogenation catalysts.

The oxo process is well known in the art and is generally described in detail in Kirk-Other, Encyclopedia of Chemical Technology, Volume 16, 3rd ed., John Wiley & Sons, pp. 637–653, 1981.

In the well known oxo process, olefins are hydroformylated by reaction with carbon monoxide and hydrogen, generally charged as syn gas mixtures, in the presence of a cobalt oxo catalyst in dissolved form to form a mixture of oxo aldehydes and alcohols. This oxo reaction is typically carried out at syn gas pressures of from about 10.33 MPa to 31.00 MPa (1500 to 4500 psig) and at temperatures of from about 65° C. to 230° C. Thereafter, the product mixture containing the alcohols and aldehydes is recovered and can then be treated by known means to hydrogenate the aldehydes to form additional quantities of the corresponding alcohols. These alcohols, in turn, are widely used as chemical intermediates in the manufacture of plasticizers, detergents, solvents and the like.

Prior to the hydrogenation step, the crude oxo reaction effluent, which contains dissolved cobalt catalysts, the aldehyde and alcohol products and reaction by-products together with any metallic contaminants, is generally treated to remove the dissolved cobalt catalyst, which then for reasons of economy must be recycled to the oxo reactor.

"Demetalled" hydroformylation reaction product or crude oxo alcohol product is the reaction product which is substantially depleted of the transition metal cobalt catalyst required for the hydroformylation reaction. Such crude oxo product will generally contain cobalt in an amount of from about 0.05 to 3.0 wt. %, calculated as elemental cobalt. The concentration of aldehyde in the crude oxo alcohol product is generally from about 40 to 75 wt. %.

The next step in the oxo process is the hydrogenation of the crude alcohol product which is typically carried out at pressures of about 6.89 MPa to 31.00 MPa (1000 to 4500 psig) using sulfided bimetallic cobalt and molybdenum oxides or nickel and molybdenum oxide supported on alumina as the hydrogenation catalyst. Because of the high content of carbonyl-containing compounds present in the crude alcohol product, the use of relatively high pressures with the traditional bimetallic catalysts has been required in order to achieve the desired yield of alcohol product.

The use of bimetallic catalysts in the hydrogenation of crude alcohol oxo product is disclosed, for example, U.S. Pat. No. 5,030,774, issued Jul. 9, 1991 and European Application 89304856.1, published Nov. 29, 1989. The present invention is based on the discovery that bimetallic nickel-molybdenum catalysts, which have a low phosphorous content (i.e., about 0.1 to 1.0 wt. %), when used in the oxo process increase the yield of alcohol product.

In accordance with the present invention there has been discovered an improvement in the process for preparing oxo alcohols by the cobalt catalyzed hydroformylation of olefins which comprises the sequential steps of (a) hydroformylating $C_5$-$C_{12}$ olefins by reaction with carbon monoxide and hydrogen in the presence of a cobalt hydroformylation catalyst (hydro cobalt carbonyl), (b) demetalling the crude reaction product of step (a) to recover therefrom homogeneous cobalt catalyst and to separate therefrom essentially cobalt-free crude alcohol product which contains 20 wt. % or more of carbonyl-containing compounds such as aldehydes, acetals, ethers and esters, (c) hydrogenating the crude alcohol product of step (b) at elevated temperatures and pressures to reduce the carbonyl-containing compounds to alcohols, (d) distilling the product of step (c) and recovery therefrom oxo alcohols containing very small proportions of carbonyl compounds, and (e) hydrofinishing (by hydrogenation) the product of step (d) to provide a substantially pure alcohol product, the improvement being characterized in that step (c) or step (e) or both may be carried out using a bimetallic nickel-molybdenum catalyst supported on alumina or silica alumina which catalyst has a phosphorous content of about 0.1 wt. % to 1.0%, based on the total weight of catalyst.

The olefin feedstock for the hydroformylation reaction is typically a commercial olefin feedstock which may include linear and branched $C_2$-$C_{17}$ monoolefins. Preferably, the olefin feedstock contains a significant amount of a branched $C_5$-$C_{12}$ monoolefin. The preferred olefins include amylenes from petroleum cracking, heptenes, octenes, nonenes and dodecenes from fractionation of oligomers of $C_3$-$C_4$ olefin, and octenes from dimerization and codimerization of isobutylene and 1- and 2-butenes.

Cobalt catalyzed hydroformylation is typically carried out at a pressure of 15-30 MPa and a temperature of about 120°–190° C. Cobalt catalyst is present in its active form as hydrido cobalt carbonyl in a concentration of from 0.05-3.0 wt. %, preferably 0.05 to 1 wt. %, calculated as metal based on olefin feedstock. The synthesis gas typically has a $H_2$:CO volume ratio in the range of 0.9:1 to 1.5:1.

After separation of the cobalt catalyst from the crude reaction product, the crude alcohol product, which is hydrogenated in accordance with this invention, will contain a substantial proportion of carbonyl-containing compounds which are produced as a result of the hydroformylation reaction. These carbonyl-containing compounds mainly include aldehydes, acetals, formates, esters and ethers, and the crude alcohol product will contain 20 wt % or more, more typically 40 to 75 wt %, of aldehydes and other carbonyl compounds which are to be hydrogenated to the desired alcohol product.

The catalysts useful in the process of the invention are prepared by impregnating molybdenum onto the alumina support using phosphomolybdic acid, $12MoO_3 \cdot H_3PO_4$, as the medium to carry the molybdenum out of the alumina or silica alumina support.

Normally in preparing such catalysts, phosphoric acid has been used as the solvent for the molybdenum salts which are impregnated onto the alumina support. This typically results in phosphorous levels of about 3 wt. % on the hydrogenation catalyst. For example, U.S. Pat. No. 5,151,257 discloses the use of a solution of nickel carbonate and molybdenum oxide in phosphoric acid to prepare a catalyst on the support and U.S. Pat. No. 4,997,801 discloses the same solution of $NiCO_3$ and $MoO_3$ in phosphoric acid (85%) to prepare a catalyst using gamma-alumina as the support.

These catalysts are also particularly preferred for use in their sulfided form after being sulfided by the techniques well known in the art using gaseous ($H_2S$) or liquid sulfiding compounds, such as ammonium or sodium sulfide solutions, to convert the oxides of the metals to their corresponding sulfides. Typically about 80% to 100% of the oxides are converted to metal sulfides in such a sulfiding procedure.

The catalysts of the present invention may be used either in the first hydrogenation step of the oxo process or in the final hydrofinishing (hydrogenation) step, or in both. When used in the first hydrogenation step, the advantage results in enabling this step to be carried out at relatively lower pressures while still achieving a desired conversion of carbonyl-containing compounds to the alcohol product. When used as the catalyst in the final hydrofinishing step, which is also a hydrogenation reaction, its advantage is that the carbonyl number (rag KOH/g) can be effectively reduced to levels less than 0.2 mg KOH/g in the finished alcohol product.

The invention is illustrated by the following examples which are not to be considered as limitative of its scope.

EXAMPLE 1

This example demonstrates alcohol yield loss sustained upon hydrogenation of crude oxo alcohol over bimetallic Ni/Mo on alumina with high (i.e., 2.85 wt. % P) phosphorous content. The hydrogenation was carried out at 6.89 MPa (1000 psig) over a temperature range of 138° C. (280° F.) to 182.4° C. (360° F.). Crude nonanal was the feedstock used for catalyst performance evaluation.

For this particular example, sulfided Ni/Mo on alumina catalyst, inerted under isodecyl alcohol, was charged as test material. Typical catalyst properties are included in Table 2, below.

Two 316 stainless steel, 1/2" diameter reactors with appropriate high pressure connectors were each charged with 65 cubic centimeters of catalyst material to be evaluated. The catalyst loaded reactors are immersed in a fluid bed, constant temperature sand-bath equipped with electrical heaters for temperature control. Appropriate mechanical connections were installed to allow reactor operation at nominal pressure of 6.89 MPa (1000 psig) and nominal test temperatures from 138° C. (280° F.) to 182.4° C. (360° F.).

Under steady state conditions liquid feed and gaseous high purity hydrogen (>99 vol.% $H_2$) are pumped over the fixed catalyst bed. Liquid and gaseous product is subsequently depressurized and sampled periodically. Aliquots of liquid product and liquid feed are analyzed for composition by gas chromatography.

The liquid feed consists of demetalled hydroformylation product of crude aldehyde. All evaluations were performed on nonanal mixed with water at nominal water/feed of 3 vol.%. Typical crude aldehyde component distribution appears in Table 1, below.

Commercially available bimetallic Ni/Mo on alumina catalyst (Cat-A), containing 2.85 weight % P, was evaluated for crude oxo aldehyde hydrogenation performance. Catalyst physical and chemical composition appear in Table 2, below.

The catalyst (Cat-A) described in Table 2 was tested at conditions listed in Table 3. Product composition for different test samples included in Table 3 was determined by gas chromatography.

Cat-A hydrogenation performance is assessed by studying aldehyde conversion as well as selectivity to undesired byproducts. Comparing product composition in Table 3 with the corresponding feed crude nonanal composition in Table 1, aldehyde conversion in excess of 95% is obtained. However, the desired product alcohol content (Table 3, Column (6)) is only between 61 wt % to 67 wt %. Lower product alcohol content results from undesired catalyst Cat-A selectivity to produce undesired heavy by-products (Table 3, Column (7)). The overall increase in heavy by-product produced by Cat-A, relative to feed composition over the temperature range under study, appears in Table 3, Column (9). Heavy-end increment, relative to feed, between 12 wt % and 19 wt %, is produced by Cat-A, indicated in Table 3 (Column (9)) and in Table 5 over the temperature range under study.

Catalyst A was prepared as follows:

Solution 1: Dissolved 104.462 grams of nickel nitrate into 50 ml deionized water and added 69.774 grams of phosphoric acid solution.

Solution 2: Added 159.609 grams of ammonium molybdate to 75 ml deionized water and added 69.774 grams of hydrogen peroxide. Stirred until dissolved. Added the ammonium molybdate solution (solution 2) to the nickel nitrate/phosphoric acid solution (solution 1). Diluted resulting mixture to 320 ml with deionized water Using the Aubin rotary impregnation vessel, impregnated solution onto 500 grams of air exposed KF-840 alumina base with 5.9 wt. % moisture content. Put sample in an evaporating dish to air dry under hood overnight.

Dried in a convection oven at 130° C. for 3.5 hours. Calcined in air for 2 hours at 427° C. (800° F.).

TABLE 1

| | Crude Aldehyde (Nonanal) Feed composition | | | |
|---|---|---|---|---|
| (1) Feed Type | (2) Lights, wt. % (Olefin + Paraffin) | (3) Aldehyde + Formate Esters, wt. % | (4) Alcohol, wt. % | (5) Heavier than Alcohol, wt. % |
| A | 7.08 | 86.30 | 2.62 | 4.00 |
| B | 7.91 | 79.07 | 3.61 | 9.41 |
| C | 8.97 | 70.76 | 4.58 | 15.69 |
| D | 8.05 | 79.68 | 3.54 | 8.73 |
| E | 7.09 | 82.83 | 3.11 | 6.97 |
| F | 6.83 | 85.89 | 2.51 | 4.77 |
| G | 6.79 | 87.37 | 2.22 | 3.61 |
| H | 7.18 | 82.57 | 3.65 | 6.61 |

TABLE 2

| | Representative Ni/Mo Catalyst Properties | | | | |
|---|---|---|---|---|---|
| Catalyst Type | Chemical Composition, Component Weight % (a) | | | Physical Properties | |
| | $MoO_3$ | NiO | P | Surface Area, m²/g | Total Pore Volume, ml/g |
| Cat-A | 20.0 | 4.0 | 2.85 | 180 | 0.45 |
| Cat-B | 20.0 | 4.0 | 0.43 | 233 | 0.37 |

(a) — Balance chemical composition: $Al_2O_3$ and $SiO_2$

TABLE 3

Summarized Nonanal Hydrogenation Test Conditions and Results (a)

| | Test Conditions | | | Product Composition | | | | Undesired Yield | |
|---|---|---|---|---|---|---|---|---|---|
| Test # | (1) Catalyst Type | (2) Feed Type | (3) Temperature, °C., °F. | (4) Lights, wt. % | (5) Ald + Form, wt. % | (6) Alc, wt. % | (7) Heavier than Alcohol, wt. % | (8) Delta Lights (b), wt. % | (9) Delta Heavier than Alcohol (c), wt. % |
| 1 | Cat-A | A | 138°, 280° | 6.82 | 3.60 | 67.02 | 22.56 | −0.26 | 18.56 |
| 2 | Cat-A | B | 149°, 300° | 7.57 | 1.47 | 65.93 | 25.02 | −0.34 | 15.61 |
| 3 | Cat-A | C | 160°, 320° | 8.08 | 1.90 | 61.67 | 28.36 | −0.89 | 12.67 |
| 4 | Cat-A | D | 182°, 360° | 9.26 | 2.03 | 66.91 | 21.80 | 1.21 | 13.07 |
| 5 | Cat-B | E | 138°, 280° | 7.11 | 1.18 | 76.89 | 14.81 | 0.02 | .7.84 |
| 6 | Cat-B | F | 149°, 300° | 7.08 | 0.92 | 78.50 | 13.49 | 0.25 | 8.72 |
| 7 | Cat-B | G | 160°, 320° | 7.21 | 0.65 | 82.48 | 9.67 | 0.42 | 6.06 |
| 8 | Cat-B | H | 182°, 360° | 7.74 | 1.55 | 80.01 | 10.71 | 0.56 | 4.10 |

(a) All tests at nominal Feed Rate of 130 ml/hr., Water Rate of 4 ml/hr., Linear Hourly Space Velocity (LHSV) of 1 ml catalyst/(ml feed/hr.). All tests conducted at 6.89 MPa (1000 psig).
(b) Calculated as: {[Product Lights Composition, Column (4), Table 3]-[Feed Lights Composition, Column (2), Table 1]}
(c) Calculated as: {[Product Heavy Composition, Colunm (7), Table 3]-[Feed Heavy Composition, Column (5), Table 1]}
Note:
In Column (5), "Ald & Form" refers to Aldehydes and Formates; in Column (6), "Alc" refers to Alcohol. In Columns (8) and (9), "Delta" refers to the difference.

EXAMPLE 2

This example demonstrates alcohol yield improvement obtained upon hydrogenation of crude oxo alcohol over bimetallic Ni/Mo on alumina with low (i.e., about 0.5 wt. % P) phosphorus content. Hydrogenation conditions were identical to those described in Example 1, above. Crude nonanal was the feedstock used for catalyst performance evaluation.

The low phosphorus content catalyst (Cat-B) described in Table 2 was produced in the laboratory out of a formulation which used phosphomolybdic acid (12MoO3.H3PO4) "PMA" to impregnate Mo salts onto the alumina support, rather than using the more traditional approach of preparing a mixture of inorganic salts of molybdenum and phosphoric acid. The use of PMA as Mo impregnating agent produces a low phosphorus content catalyst with high Mo dispersion.

For this particular example, the laboratory prepared Cat-B was sulfided with H2S as described below.

LABORATORY SULFIDING PROCEDURE

A 316 stainless steel, 1/2" diameter reactor, is charged with 65 cubic centimeters of catalyst oxide material to be sulfided. The catalyst loaded reactor is placed inside a vertical heater equipped with temperature control capability. The reactor is connected to a gas manifold which can deliver controlled rates of gas flow. High purity nitrogen (>99 volume % N2) and a hydrogen sulfide/hydrogen blend are required.

The following sulfiding procedure is followed at atmospheric pressure, with 10 volume % H2S in hydrogen blend as sulfiding gaseous agent:

a- Establish nitrogen flow at 100 cc/min. over catalyst oxide bed at room temperature (approximately 80° F.). Under nitrogen flow, increase reactor temperature to 199 ° C. (390° F.) and maintain at temperature for 1 hour.

b- While maintaining reactor temperature at 199° C. (390° F.), substitute nitrogen with 10 vol.% H2S/H2 blend gas at 100 cc/min. flow rate. Maintain H2S blend at 199° C. (390° F.) for 2 hours. Under 10 vol.% H2S/H2 blend, increase reactor temperature to 339° C. (643° F.) and maintain at temperature for 12 hours.

Substitute 10 vol.% H2S/H2 blend with nitrogen at 100 cc/min. flow rate. Cool reactor to room temperature (approximately 80° F.) under nitrogen flow. Isolate reactor, now containing sulfided catalyst, under a nitrogen atmosphere and transfer to sand-bath, in order to evaluate hydrogenation activity.

The low phosphorus Ni/Mo catalyst (Cat-B) described in Table 2 was evaluated at conditions listed in Table 3, Product composition for different test samples in Table 3 was determined by gas chromatography.

Evaluation of Low-Phosphorous Content Catalyst (Cat-B)

Similar to Example 1, Cat-B hydrogenation performance is assessed through evaluation of aldehyde conversion as well as selectivity to undesired by-products. Comparing product composition in Table 3 with the corresponding feed crude nonanal composition in Table 1, aldehyde conversion in excess of 98% is attained. In comparison with Cat-A performance (described in Example 1, above), superior aldehyde conversion is obtained with the low phosphorous catalyst (Cat-B) over the temperature test range.

Improved aldehyde conversion is further accompanied by improved selectivity to the desired alcohol product, resulting from reduced undesired heavy by-product formation, relative to Cat-A. Improved selectivity is determined by comparison of the undesired heavy by-product in Table 3 (Column (9)) obtained for Cat-B (varying from 4 wt. % to 9 wt. % over the temperature range under study), relative to heavy production by Cat-A (varying from 12 wt. % to 19 wt. % over the identical temperature range as Cat-B). Table 5 illustrates the relative undesired heavy byproduct yield for both catalysts Cat-A and Cat-B.

Reduced heavy by-product obtained by Cat-B results in corresponding product alcohol gain. Improved alcohol yield is calculated by subtracting the value in Column 4 of Table 1 from the value in Column 6 of Table 3 and presenting the results in Table 4. Thus Cat-B produced alcohol yield improvements, relative to Cat-A, in the range from 9 wt. % to 23 wt.% as indicated in Table 4.

Catalyst B was prepared as follows:

Added 39.237 grams of nickel carbonate, 69.29 grams of citric acid, and 164.971 grams of Fisher phosphomolybdic acid to the bottom of a beaker and dry mixed. Slurried this mixture by adding 130 ml of deionized water. Stirred and heated to boiling. Continued heating until bubbles stopped. After boiling allowed solution to cool to room temperature. Diluted solution to 320 ml with deionized water. Using the Aubin rotary impregnation vessel, impregnated the solution onto 500 grams of KF-840 alumina base (reference number 84VA-0687) with 5.9 wt. % moisture content. Put sample in an evaporating dish to air dry under hood overnight.

Dried in convection oven at 130° C. for 3.5 hrs. Calcined in air for 2 hours at 427° C. (800° F.).

TABLE 4

Summarized Nonanol Yield Improvement Obtained with Low P Ni/Mo Catalyst (Cat-B) Relative to Commercial High P Catalyst (Cat-A)

| Test Number | (1) Feed Type | (2) Temperature °C., °F. | (3) Cat-B Alcohol Yield Improvement wt. % |
|---|---|---|---|
| 1 | E | 138°, 280° | 9.4 |
| 2 | F | 149°, 300° | 13.7 |
| 3 | G | 160°, 320° | 23.2 |
| 4 | H | 182°, 300° | 13.0 |

TABLE 5

Effect of Phosphorous Content on Ni/Mo Catalyst Performance for Crude Nonanal Hydrogenation Yield Increase of Undesired By-Products

| Test Temperature | Cat-A | Cat-B |
|---|---|---|
| 138° C., 280° F. | 18.5% | 8% |
| 149° C., 300° F. | 15.7% | 9% |
| 160° C., 320° F. | 12.5% | 6% |
| 182° C., 360° F. | 13.0% | 4% |

Test Condition: 6.59 MPa (1000 psig), 1 LHSV and 3 vol. %. $H_2O$/Nonanal
Note:
"Yield Increase and Undesired By-Products" refers to the increase in products which are of a molecular weight which is greater than the desired nonanal product.

What is claimed is:

1. In the process for preparing oxo alcohols by the cobalt catalyzed hydroformylation of olefins, which process comprises the sequential steps of:
   (a) hydroformylating of olefins by reaction with carbon monoxide and hydrogen in the presence of a cobalt hydroformylation catalyst to produce a crude reaction product;
   (b) demetalling the crude product of step (a) to recover therefrom homogeneous cobalt catalyst and separate therefrom crude alcohol product, the crude alcohol product containing 20 wt. % or more of carbonyl compounds;
   (c) hydrogenating the crude alcohol product at an elevated temperature and pressure to reduce the carbonyl compounds to alcohols;
   (d) distilling the product of step (c) and recovery therefrom alcohol products containing very small proportions of carbonyl compounds; and
   (e) hydrofinishing the product of step (d) to provide a substantially pure alcohol product, the improvement which comprises conducting step (c) or (e), or both, in the presence of a Ni/Mo hydrogenation catalyst supported on alumina or silica alumina which has been prepared by impregnating the support with phosphomolybdic acid, the catalyst having a phosphorous content of 0.1 to 1.0 wt. %.

2. The process of claim 1 wherein the catalyst support is silica-alumina.

3. The process of claim 1 or 2 wherein the catalyst is sulfided.

4. The process of claim 1 wherein the catalyst has a phosphorous content of about 0.5 wt. %.

* * * * *